United States Patent [19]

Rowland

[11] 4,046,722

[45] Sept. 6, 1977

[54] IMMUNOLOGICAL MATERIALS

[75] Inventor: George Ferdinand Rowland, Gerrards Cross, England

[73] Assignee: G. D. Searle & Co. Limited, Bucks, England

[21] Appl. No.: 648,841

[22] Filed: Jan. 14, 1976

[30] Foreign Application Priority Data

Feb. 4, 1975 United Kingdom .................. 4696/75

[51] Int. Cl.$^2$ ............................................. C08L 89/00
[52] U.S. Cl. ........................................ 260/6; 424/55; 260/112 B; 260/112 R; 260/121
[58] Field of Search ......... 424/85; 260/112 R, 112 G, 260/6, 112 B

[56] References Cited

PUBLICATIONS

Sela et al., "Studies on . . . of Proteins", Biochem. Journal, 1962, vol. 85, pp. 223–235.

*Primary Examiner*—Lewis Gotts
*Assistant Examiner*—Cary Owens
*Attorney, Agent, or Firm*—John J. McDonnell

[57] ABSTRACT

The present invention is concerned with a cytotoxic agent comprising an immunoglobulin specific for antigens on the surface of the cell to be killed having 1–10 polymer carrier molecules covalently bonded thereto and the polymer carrier having 5–500 molecules of a cytotoxic drug covalently bound. The compounds of the present invention are useful as anti tumor agents.

13 Claims, No Drawings

IMMUNOLOGICAL MATERIALS

The present invention encompasses a cytotoxic agent comprising an immunoglobulin specific for antigens on the surface of cells to be killed having 1-10 polymer carrier molecules covalently bound thereto, said polymer carrier having about 5-500 molecules of a cytotoxic drug covalently bound thereto and said polymer carrier having a molecular weight of 5000-500,000 and free carboxyl, amino or cycloimidocarbonate groups for covalently bonding, said cytotoxic drug also having amino or carboxyl groups available for covalent bonding.

Cytotoxic agents of the present invention are represented by the formula A

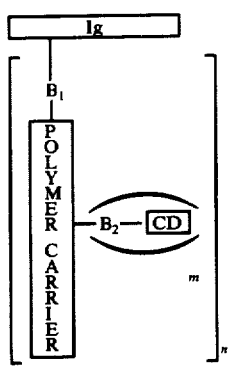

wherein Ig represents an immunoglobulin specific to antigens on the surface of cells to be killed; the polymer carrier has a molecular weight of 5000-500,000 and is selected from the group of polymers comprising:

a. dextran activated with cyanogen bromide to form cycloimidocarbonate and functionalized with —NH(CH$_2$)$_x$CO$_2$H, or —NH—(CH$_2$)$_x$—NH$_2$, wherein $x$ is 3-8,
b. aminoethylated dextran,
c. polyglutamic acid
d. polyaspartic acid,
e. polyarginine,
f. serum albumen,
g. fibrinogen,
h. γ-globulin,
i. polylysine (solubilized by reaction with citraconic anhydride),
j. copolymers of lysine-phenylalanine, lysine-tyrosine, and glutamic acid-tyrosine;

CD represents a covalently bound cytotoxic drug selected from the group comprising:

p-[N,N-bis(2-chloroethyl)]phenylenediamine,
p-[bis(2-chloroethyl)amino]phenylalanine,
4-p-[bis(2-chloroethyl)amino]phenyl butyric acid,
2-amino-N-[p-bis(2-chloroethyl)amino]phenyl-3-hydroxypropionamide,
2-amino-N-[p-bis(2-chloroethyl)amine]phenyl-3- hydroxy-2-hydroxymethyl propionamide,
N-{p{[(2,4-diamino-6-pteridinyl)methyl]methylamino}- benzyl}-L-glutamic acid,
cytosine arabinoside, cytosine arabinoside monophosphate,
0-[N,N-bis(2-chloropropyl)]carbamoylglycollic acid, daunomycin, doxorubicin, and diphtheria toxin;

B$_1$ represents a covalent bond between Ig and polymer carrier of the formula

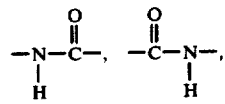

B$_2$ represents a covalent bond between the polymer carrier and CD of the formula

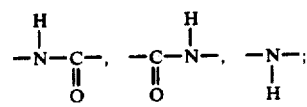

$m$ = 5-500;
$n$ = 1-10.

Polymer carriers of the present invention have a molecular weight range of between 5000 and 500,000 and are functionalized so as to react with both cytotoxic drugs and amino or carboxylic acid groups of immunoglobulins. Suitable polymer carrier and funcitonal binding groups are polypeptides having free amino or carboxyl group for bonding such as: polyglutamic acid (carboxyl), polylysine (amino), polyethyleneimine(amino), polyaspartic acid (carboxyl), polyarginine (amino); copolymers such as:

glutamic acid-tyrosine (carboxyl)
lysine-phenylalanine (amino)
lysine-tyrosine amino;

polypeptidyl proteins and multichain polyamino acids (carboxyl and amino) as described by Sela et al., Biochem J. 85 223 (1962);

proteins such as:

| human serum albumin  human fibrinogen  human γ-globulin | carboxyl and amino |

Also suitable are functionalized dextrans such as aminoethylated dextran as described by Harding, Am. N.Y. Acid. Sci. 186, 270 (1971) (amino). Dextran activated with cyanogan (amino or carboxyl) broxmide and functionalized with H$_2$N—(CH$_2$)$_x$—NH$_2$ or H$_2$)$_x$—CO$_2$H to form dextrans represented by:

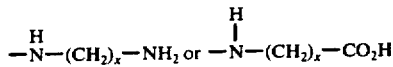

wherein $x$ is 3-8, preferably 6. The cyanogen bromide forms a reactive cycloimidocarbonate

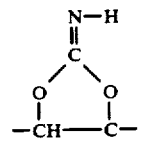

when reacted with dextran.

It is generally preferred to have only 1-10 polymer carriers covalently linked to the Ig so as not to disturb the antibody activity of the Ig. In this manner the immunoglobulin specifically directs or homes large volumes of cytotoxic drug to the surface of the cell to be killed.

Cytotoxic drugs useful for practicing the present invention are as follows:

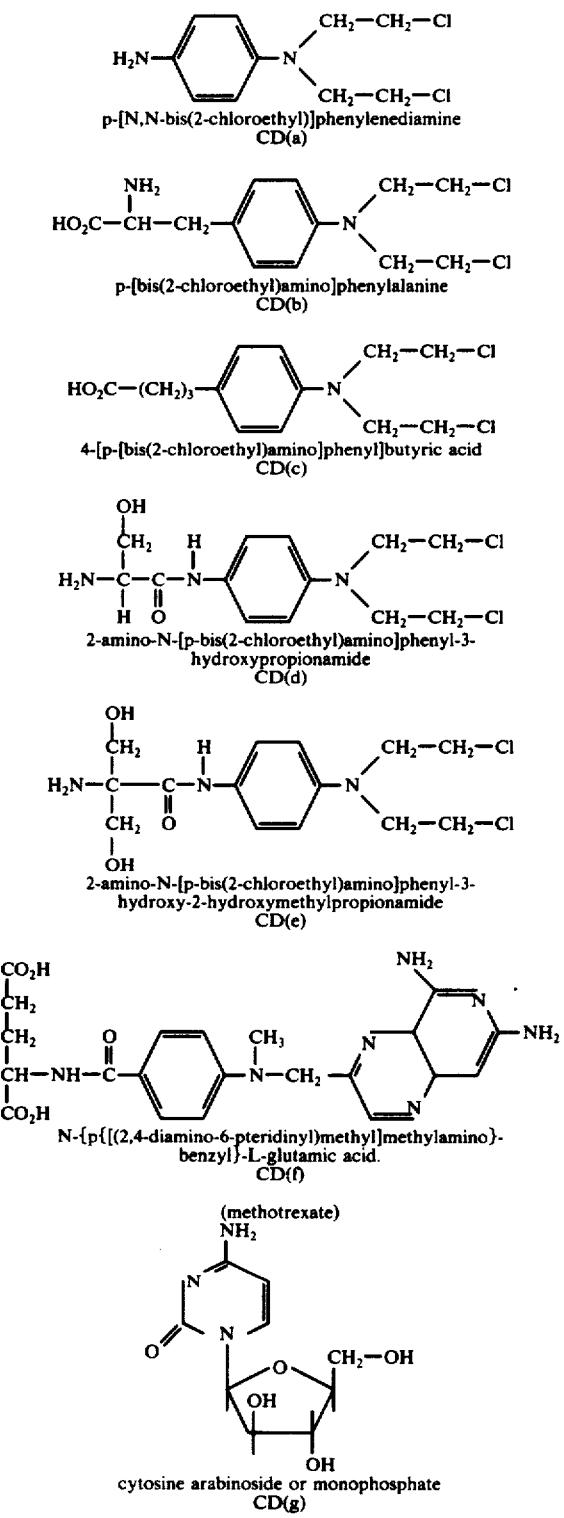

The above are preferred agents against neoplastic disease. 5-Fluorodeoxyuridine, o-(N,N-bis-2-chloropropyl)-carbamoylylycollic acid, daunomycin, doxorubicin, and diptheria toxin are likewise useful. It is, however, to be recognized that other cytotoxic drugs with suitable functional groups can be bound to polymer carriers which, in turn, are bound to an immunoglobulin. The latter serving as a means of directing the drug to the cell to be killed.

The bond between the cytotoxic drug and the polymer carrier should be such that the cytotoxic drug is cleaved enzymatically on the target cell surface. The peptide bond is especially preferred since proteases are on cell surfaces and therefor the cytotoxic drug which is peptide bound to a polymer carrier which in turn is bound to Ig can be selectively delivered to the surface of the cell to be killed and then released to provide a high concentration of cytotoxic drug at the target cell.

Structures of immunoglobulins are remarkably similar, Science 189, 1075 (1975), in that gross structural features and amino acid content varies only slightly from one immunoglobulin to another.

Immunoglobulins specific to antigens on the surface of cells to be killed and techniques for their production are known. Some representative immunoglobulins are:

a. goat anti-CEA Ig from human colonic adenocarcinoma, Hsu-Fu Chao et al., Res. Comm. in Chem., Path, and Pharmacol 9, 749 (1974).

b. Ig from rabbit anti-acute lymphoblastic leukemia serum, Greaves et al., Clin. Immunol. and Immunopath. 4, 67 (1975).

c. Ig from various primate anti-leukemia antisera, anti-acute lymphoblastic leukemia, acute myleoblastic leukemia, chronic lymphoblastic leukemia, and chronic granulocytic leukemia, all as described by Mohanakumar, et al., J. Nat. Cancer Inst. 52, 1435 (1974).

d. human anti-human meningioma Ig., Winters and Rich, Int. J. Cancer 15, 815 (1975).

e. rabbit anti-human prostate Ig, Moncure et al., Cancer Chemotherapy Reports 59, 105 (1975).

f. rabbit anti-human chorionic gonadotropin serum g. goat anti-human lymphoid cell Ig.

h. rabbit anti-mouse (EL4) lymphoid cell Ig.

i. Ig against lymphocyte surface antigens for example Ia antigens. Staines et al., Tissue Antigens 393 (1975).

j. Ig against surface antigens on antibody producing cells.

k. Ig against fungal cell surface antigens. Fukazawa et al., J. Bact. 95 754 (1968).

l. Ig against Bacterial cell surface antigens.

m. Ig against antigen on the surface of cells involved in inflammatory response.

Polymer carriers are covalently bound to the above set out immunoglobulins by way of free carboxyl or amino groups on the immunoglobulin. Water soluble carbodiimides such as 1-ethyl-3-(3-dimethylaminopropyl)-carbodiimide conveniently forms a peptide bond between a carboxyl group on the immunoglobulin and an amino group on a polymer carrier or between an amino group on the immunoglobulin and a carboxyl containing polymer carrier. Alternatively immunoglobulins (Ig) are covalently linked to polymer carriers having free amino groups by condensation with glutaraldehyde, a diimide linkage as shown in the following scheme.

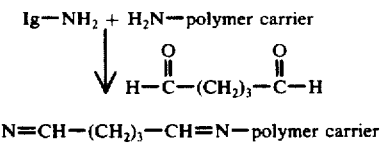

Some preferred embodiments of the present invention are set out in the formula B:

-continued

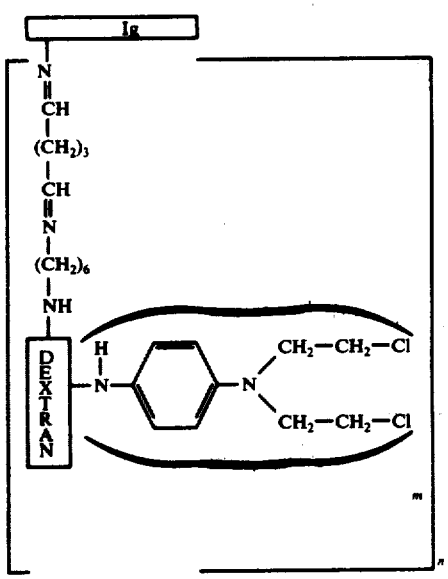

wherein $m$ is 5–100, $n$ is 1–10 and dextran molecular weight, 500–500,000, preferably 5000–50,000 and most preferably 15,000–20,000, activated by cyanogen bromide and functionalized with 1,6-diaminohexane. 17,000 is a very desirable molecular weight and $H_2N-(CH_2)_6-NH_2$ can be replaced with $-(CH_2)_x-\bar{x} = 3-8$.

In a similar manner cytotoxic drugs, CD(b), CD(d), and CD(e) are bound to dextran as polymer carrier and $m$, $n$, $x$ and molecular weight variables are the same as in B.

C represents another preferred embodiment:

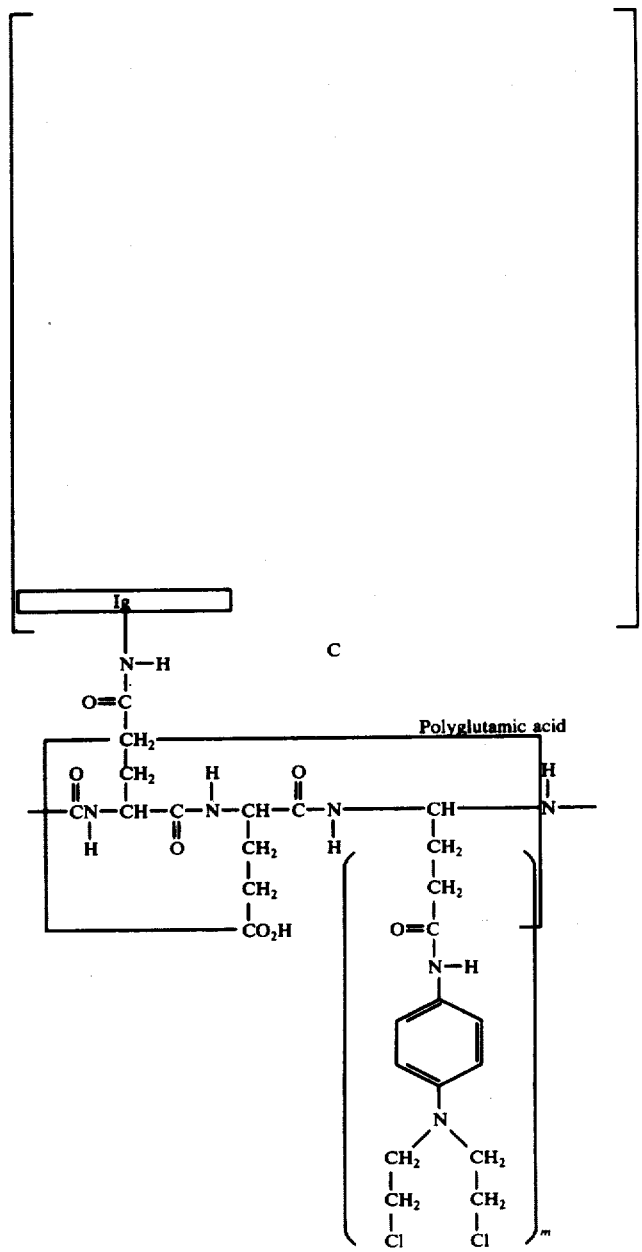

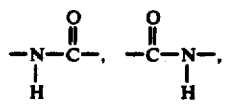

wherein $m$ is 5–100, $n$ is 1–10, the polymer carrier is polyglutamic acid having a molecular weight of 5,000–500,000, preferably 5,000–100,000, and most preferably about 35,000; or C' using CD(b) is preferred:

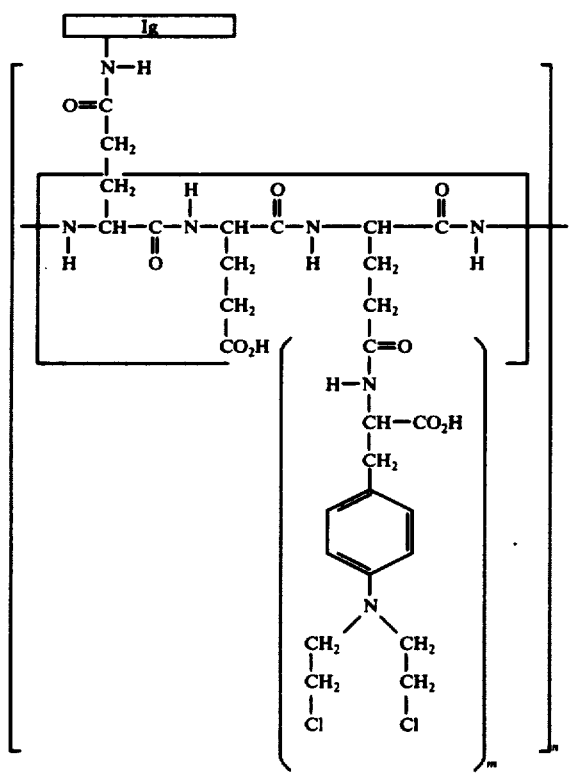

C' wherein $m$, $n$ and molecular weight of the polyglutamic acid is as described above in C.

In a similar manner cytotoxic drugs (d) and (e) (C" and C''') are bound to polyglutamic acid wherein the molecular weight parameters of the polymer carrier, $m$, and $n$, are as earlier defined in C. The peptide linkages are preferably achieved by use of 1-ethyl-3-(3-dimethylaminopropyl)carbodiimide. Generally 10–100 CD are bound to each Ig by way of the polymer carrier.

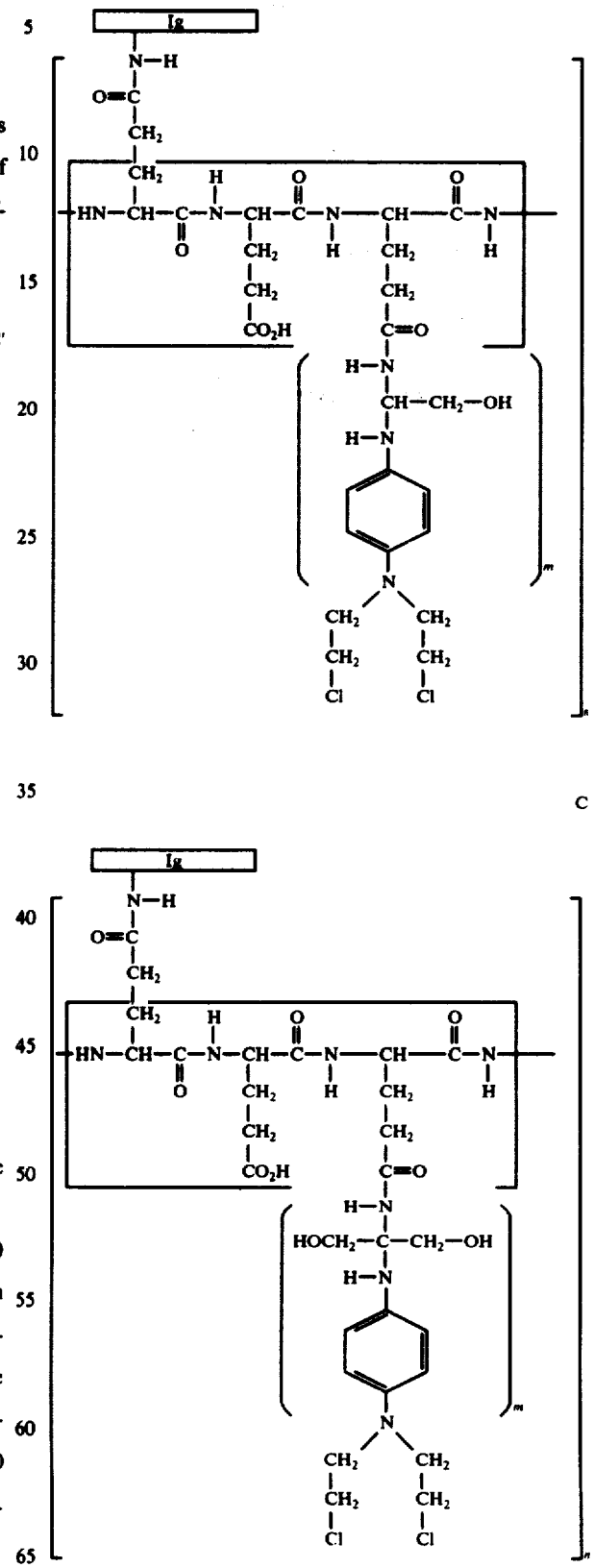

C"

D represents another preferred embodiment

D

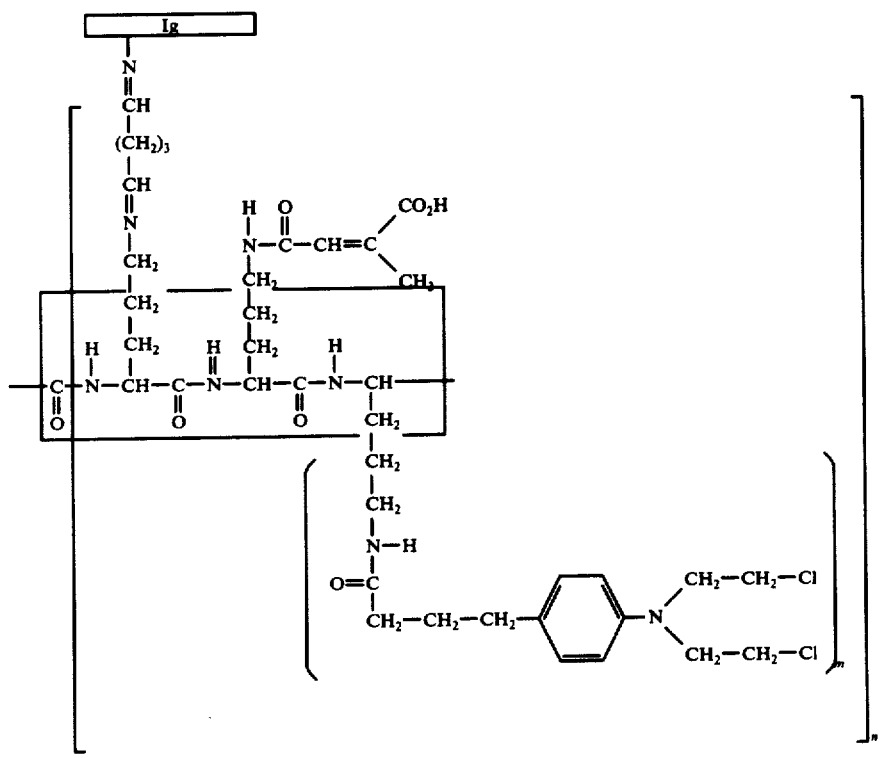

wherein m is 5–100, n is 1–10, and the molecular weight of the polylysine polymer carrier is 5,000–500,000, preferably 5000–100,000. The cytotoxic drug (b) or (f) may be used in place of 4-{p-[bis(2-chloroethyl)amino]-phenyl}butyric acid. In addition a preferred embodiment is obtained fixing the parameters in formula D as shown and replacing polylysine with polyethylenimine of the above set out molecular weight range with molecular weight 20,000 being especially preferred. Free amino groups on the polymer carrier can be reacted further with citraconic acid anhydride to function the amide and aid in solubility of the cytotoxic agent.

Table I illustrates preferred embodiment of the present invention.

TABLE 1

| Ig | $B_1$ | $B_2$ | Polymer Carrier | CD |
|---|---|---|---|---|
| | −N−C−<br>H  ‖<br>   O | −C−N−<br>‖  H<br>O | Polyglutamic acid | a,b,d,e |
| | −C−N−<br>‖  H<br>O<br>or<br>−N=CH−(CH$_2$)$_3$−CH=N−<br>−C−N−<br>‖  H<br>O<br>or<br>−N=CH−(CH$_2$)$_3$−CH=N− | −N−C−<br>H  ‖<br>   O | Polylysine<br>M.W. 5000–100,000<br>solabilized by reaction<br>with citraconic anhydride | b,c,f |
| | | −C−C−<br>H  ‖<br>   O | Polyethyleneimine<br>M.W. 5,000–100,000 | b,c,f |
| | −C−N−<br>‖  H<br>O<br>or<br>−N=CH−(CH$_2$)$_3$−CH=N−<br>−C−N−<br>‖  H<br>O | −N−C−<br>H  ‖<br>   O | aminoethylaled dextran | b,c,f |
| | | −N−<br>H | dextran activated with<br>CNBr and functionalized<br>with | b,c,f |

TABLE 1-continued

| Ig | B₁ | B₂ | Polymer Carrier | CD |
|---|---|---|---|---|
| | or $-N=CH-(CH_2)_7-CH=N-$ $\begin{array}{c}C\\\parallel\\-N-C-\\\vert\\H\end{array}$ | $\begin{array}{c}-N-\\\vert\\H\end{array}$ | $H_2-N-(CH_2)_6-NH_2$ dextran activated with CNBr and functionalized with $H_2-N-(CH_{26}-CO_2H$ | a,b,d,e |

The present invention also encompasses polymer carriers suitable for binding to immunoglobulin having a molecular weight between 5,000 and 500,000 and having 5–500 molecules of cytotoxic drug covalently bound thereto. These embodiments of the present invention are represented by the following formula:

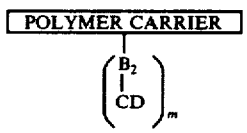

where the terms polymer carrier, $B_2$, CD, and $m$ are as previously defined.

A preferred embodiment of polymer carrier is polyglutamic acid having a molecular weight of 5,000–100,000, most preferably 35,000;

B 2 is

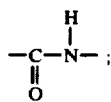

CD represents p-[N,N-bis(2-chloroethyl)]-phenylenediamine, p-[bis[2-chloroethyl)amino]-phenylalamine, 2-amino-N-[p-bis(2-chloroethyl)amino]-phenyl-3-hydroxypropionamide, or 2-amino-N-[p-bis(2-chloroethyl)amino]phenyl-3-hydroxy-2-hydroxymethyl propionamide;

Another preferred embodiment is dextran activated with cyanogen bromide and functionalized with 1,6-diaminohexane having a molecular weight of 5,000–100,000, most preferably 17,000, B₂ is

CD represents p-[N,N-bis(2-chloroethyl)]-phenylenediamine, p-[bis(2-chloroethyl)amino]-phenylalanine, 2-amino-N-[p-bis(2-chloroethyl)amino]-phenyl-3-hydroxypropionamide, or 2-amino-N-[p-bis(2-chloroethyl)amino]phenyl-3-hydroxy-2-hydroxymethyl propionamide; and $m = 5-100$.

Another preferred embodiment is aminoethylated dextran having a molecular weight of 5,000–500,000 in which CD represents p-[bis(2-chloroethyl)amino]phenylalanine or 4-{p-[bis(2-chloroethyl)amino]phenyl}butyric acid,

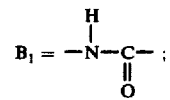

and $m = 5-100$

Another preferred embodiment is polylysine, molecular weight of 5,000–100,000, reacted with citraconic acid anhydride in which CD represents p-[bis(2-chloroethyl)amino]phenylalanine, 4-{p-[bis(2-chloroethyl)amino]phenyl}butyric acid, or N-{p{[(2,4-diamino-6-pteridinyl)methyl]methylamino}benzyl}-L-glutamic acid;

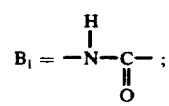

and $m = 5-100$.

Also preferred is polyethyleneimine having a molecular weight of 5,000–100,000, most preferably 20,000 in which CD represents p-[bis(2-chloroethyl)amino]phenylalanine, 4-{p-[bis(2-chloroethyl)amino]phenyl}butyric acid, or N-{p{[(2,4-diamino-6-pteridinyl)methyl]methylamino}benzyl}-L-glutamic acid;

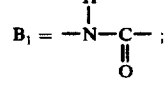

and $m = 5-100$.

Compounds of the present invention are preferably administered intravenously and they are especially advantageous by reason of their low toxicity. For example, p-[N,N-bis(2-chloroethyl)]phenylenediamine unbound has an $LD_{50}$ of 5 compared to an $LD_{50}$ of 200 for that compound bound to polyglutamic acid. Dosages of compounds of the present invention can be based on dosages of known cytotoxic agents. For example (Melphalan) p-[N,N-bis(2-chloroethyl)amino]-phenylalanine is recommended at a dose of 6 mg daily for 2–3 weeks whereas 1–20 times of this drug bound to a polymer carrier according to the present invention for a like period of time would constitute an effective dose. In a similar manner (chloroambacil) 4-{p-[bis(2-chloroethyl)amino]phenyl}butyric acid is recommended at 0.1–0.2 mg/kg/day for 3–6 weeks. That dosage can be increased up to 20 times when bound according to methods of the present invention. Compounds of the present invention preferably administered in a suitable manner by intraperitaneal injection of a dose having 0.1–0.2 mg/kg/day of cytotoxic agent bound to the polymer carrier and immunoglobulin to a warm blooded animal. The utility of the present compound is further disclosed in the hereinafter set forth examples.

The following examples are presented to further illustrate the present invention. They should not be construed as limiting it either in spirit or in scope. In these examples quantities are indicated in parts by weight unless parts by volume are specified, and temperatures are indicated in degrees Centigrade (° C). The relationship between parts by weight and parts by volume is the same as that existing between grams and milliliters.

EXAMPLE 1

500 Mg of dextran (Molecular Weight 17,700) is dissolved in 500 ml of distilled water and the pH is adjusted to 11.0 with sodium hydroxide. 400 Mg of cyanogen bromide in 1.6 ml of acetonitrile is added to the dextran solution dropwise with rapid stirring at 23° C. This mixture is stirred for 10 minutes with the pH maintained at 11.0 by addition of sodium hydroxide and then 100 mg of diaminohexane dissolved in 2.5 ml of water is added with stirring; the pH is lowered to 9.0 with hydrochloric acid and stirring is continued for 5 minutes. This procedure provides dextran having three hydroxyl groups functionalized with

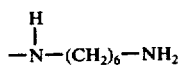

To this functionalized dextran solution is added dropwise a solution of 250 mg of p-[N,N-bis(2-chloroethyl)]-phenylenediamine hydrochloride in 5 ml of ethanol containing 2% w/v hydrochloric acid and diluted with 250 ml of 60% aqueous polylene glycol containing 1.2% w/v potassium hydrogen phosphate. During the addition the pH is allowed to fall to 6.5 and is maintained at that level by the addition of sodium hydroxide. The mixture is stirred for 15 minutes at 23° C, cooled to 4° C, and transferred to membrane ultra filtration apparatus for diafiltration with water. Diafiltration is continued until the effluent is free of uncombined p[N,N-(bis(2-chloroethyl)]phenylenediamine. The solution is concentrated by ultrafiltration to 1/5 the reaction volume and then freeze dried to provide dextran having 3 hydroxyls functionalized with

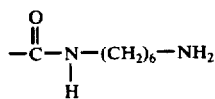

and about 15 molecules of p-[N,N-(di-2-chloroethyl)-phenylelediamine mustard bound as

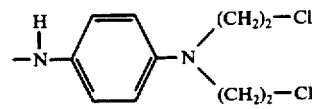

This functionalized dextran polymer having N,N-[bis(2-chloroethyl)]phenylenediamine covalently linked thereto is then bound to immunoglobulin (Ig) specific to the cell to be killed—for example, rabbit antiserum against mouse lymphoma cells (EL4) made specific by repeated absorption with normal mouse spleen cells, Br.J. Cancer 30 297-304 (1974).

6 Ml of phosphate buffered saline pH 7.2 containing 180 mg of functionalized dextran polymer carrier is mixed with 6 ml of the same buffer containing 18 mg of rabbit anti mouse EL4 lymphoma Ig. To this solution is added 1.2 ml of 0.1% w/v glutaraldehyde in 12 × 0.1 ml increments over a 5 minute time period. The mixture is rotated at 4° C for 30 minutes, then centrifuged at 35,000 × g for 10 minutes and the supernate discarded. The precipitate is resuspended in 25 ml of 40% ammonium sulfate and recentrifuged as above. The precipitate is redissolved in 4 ml of phosphate buffered saline and dialysed exhaustively to remove ammonium sulfate.

The resulting cytotoxic agent — polymer carrier — Ig, is characterized as having 31 mg/ml of protein Folin and Cioculteau, J. Biol. Chem. 73 627 (1927), and the alkylating activity is determined by the method of Espstein et al. J. Analyt. Chem. 27 1435-1439 (1955), to be 2.25 mg/ml for the dextran carrier-cytotoxic agent moiety. Thus the complex contains 36 p-[N,N-bis(2-chloroethyl)]phenylenediamines per Ig, indicating about 2 dextran carriers per Ig.

To show the effectiveness of the complex as an antitumor agent in vivo several groups of five C56BL/6 mice were inoculated with 5 × 10⁴EL4 cells intraperitoneally. This is approximately 10,000 times the LD$_{50}$ challenge dose. After 24 hours the mice receive the first of four daily injections of the complex or controls. The results are shown in the following table.

| Treatment | Dose per Injection | | Median Survival Time (Days) | % Mice Free of tumor at day 60 |
|---|---|---|---|---|
| | Drug Alkylating activity μg/injection | Ig in (mg) | | |
| Saline | — | — | 13 | 0 |
| RIg alone | — | 6.2 | 25 | 20 |
| PDM-DEX | 450 | — | 16 | 0 |
| + { PDM-DEX RIg unlinked } | 450 | 6.2 | 28 | 0 |
| PDM-DEX-RIg | 450 | 6.2 | >60 | 100 |

P M = p-[N,N-bis(2-chloroethyl)]phenylenediamine (CDa)
DEX = dextran polymer carrier activated with CNBr and functionalized with H₂N-(CH₂)₆-NH₂
RIg = rabbit antiserum against mouse ELA lymphoma

EXAMPLE 2

Following the procedure set out in Example 1 and replacing p-[N,N-bis(2-chloroethyl)]phenylenediamine with an equivalent quantity of p-[bis(2-chloroethyl)amino]phenylalanine provides a polymer carrier having a cytotoxic drug bound thereto as

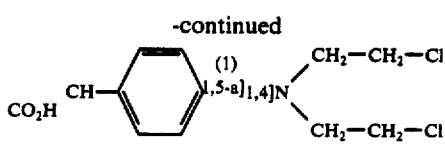

In a similar manner and using an equivalent quantity of 2-amino-N-[p-bis(2-chloroethyl)amino]phenyl-3-hydroxypropionamide provides dextran having a cytotoxic drug bound thereto as

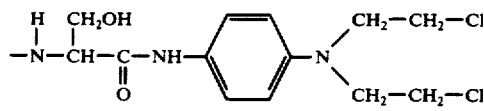

Using an equivalent quantitity of 2-amino-N-[p-bis(2-chloroethyl)amino]phenyl-3-hydroxy-2-hydroxymethyl propionamide provides a dextran polymer carrier having cytotoxic drug bound as:

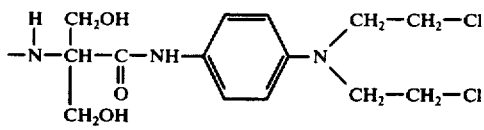

Also following the procedures in Examples 1 and 2 for binding rabbit anti sera against mouse EL4 any of the following known Ig may be bound to a like manner using equivalent quantities.

a. Goat anti-CEA Ig from human colonic adenocarcinoma, Hsu. Fu Chao et al., Res. Comm. in Chem. Path. and Pharmacol. 9, 749 (1974).

b. Ig from rabbit anti-acute lymphobastic leukemia serum, Greaves et al., Clin. Immunol. and Immunopath. 4 67 (1975).

c. Ig from various primate anti-leukemia antisera, anti-acute lymphoblastic leukemia, acute myleoblastic leukemia, chronic lymphoblastic leukemia, and chronic granulocytic leukemia cell as described by Mohanakumar et al., J. Nat. Cancer Inst. 52, 1435 (1974).

d. Human anti-Human meningioma Ig. Winters and Rich, Int. J. Cancer 15, 815 (1975).

e. Rabbit anti-human prostrate Ig, Moncure et al., Cancer Chemotherapy Reports 59 105 (1975).

f. Rabbit anti-human chorionic gonadotropin serum.

EXAMPLE 3

Preparation of Drug-Carrier (PDM - PGA)

p-[N,N-(bis-2-chloroethyl)]-phenylenediamine — polyglutamic acid 1. 250 mg polyglutamic acid PGA(m.wt. 35,000) is dissolved in water by addition of 1N NaOH dropwise until all of the PGA is in solution. The pH is adjusted to 7.0 by the addition of 1N NaOH dropwise until all of the PGA is in solution. The pH is adjusted to 7.0 by the addition of 1N hydrochloric acid if necessary. (The PGA used is polyL- glutamic acid).

2. 1g of 1-Ethyl-3-(3-dimethylaminopropyl)carbodiimide (EDC) is added to the PGA solution at room temperature.

3. 140 mg of PDMp-[N,N.(bis-2-chloroethyl)]-phenylenediamine-HCl is dissolved in 3.5 ml ethanol containing 2% w/v hydrochloric acid and is diluted with 10.5 ml 60% aqueous propylene glycol containing 1.2% w/v $K_2HPO_4$.

4. The above PDM solution is added dropwise to the stirred PGA and EDC mixture, the pH being maintained at from 6 to 7 by the addition of sodium hydroxide where necessary.

5. The above mixture is cooled to 4° C and an equal volume of cold 0.2 M Na-acetic acid buffer [pH 4.0] is added.

6. The white gelatinous precipitate formed is centrifuged cold and washed by three repeated suspensions and centrifugations in cold acetate buffer.

7. The washed precipitate is re-dissolved in 1N NaOH to a final volume of 5 ml, adjusting the pH to 7 where necessary with 1N hydrochloric acid.

The drug/carrier combination has the following characteristics:

1. The preparation is soluble in water above pH 4.5.

2. When scanned in the U.V. range the preparation has an absorption maximum at 277 nm due to the presence of covalently bound PDM ($\gamma$max of free PDM is 258 nm). From the extinction of PDM the degree of substitution of PDM molecules per PGA molecule is calculated at approximately 50:1.

3. The 'mustard' moiety is shown to be present by determination of alkylating activity of the preparation. This is done by reacting the preparation with nitrobenzylpyridine in acetone at 80° C and measuring the intensity of blue dye formed, by spectroscopy (Epstein J, Rosenthal, R. W. and Ess, R.J. Anal. Chem. 27, 1435 (1955).

4. When chromatographed on ion-exchange resins the preparation shows polyanionic behavior indicating the presence of free carboxyl residues remaining on the carrier. E.G. on DEAE Sephadex A50 or QAE Sephadex A50 eluted with a gradient from 0.1 M Tris-HCl pH 6.5 to 1M sodium chloride, the preparation shows a peak elution profile at a concentration of 0.43 M sodium chloride.

Method of Linking Drug-Carrier to immunoglobulin

1. The PDM-PGA solution is concentrated by membrane ultrafiltration to 200 mg/ml.

2. 0.6 ml is allowed to react with 20 mg EDC at room temperature for 2 minutes, then diluted to 20 ml with phosphate-buffered saline pH 7.2.

3. The diluted solution is gradually added to an equal volume of a stirred solution of rabbit immunoglobulin (RIg) as described in Example 1 at 5 mg/ml in 0.9% sodium chloride. This immunoglobulin preparation is obtained from antiserum to mouse lymphoma cells (EL4) extensively absorbed to remove antibody to normal mouse tissues.

4. 1.2 ml of 5M dodium acetate is added to quench any excess EDC remaining.

5. The PDM-PGA-RIg preparation is dialysed overnight against 0.9% sodium chloride at 4° C.

6. The preparation is concentrated by membrane ultrafiltration to a final volume of 10 ml.

The drug-carrier-globulin preparation has the following chemico-physical properties:

1. Ethanol precipitability. 0.1 ml of ethanol is added to 0.1 ml of the PDM-PGA-RIg preparation, to 0.1 ml PDM-PGA at the same concentration. After 20 minutes at room temperature the samples are centrifuged at 2500 rpm for 10 minutes on a bench centrifuge and the supernatants diluted for U.V. spectroscopy. From the U.V.

readings, the percentages of PDM-PGA and RIg precipitated are calculable:
PDM-PGA alone — 0%
R-Ig alone — 80%
PDM in PDM-PGA-RIg — 61%
Hence 61% of the drug-carrier is precipitated with 80% of the RIg. suggesting 76.5% of the drug-carrier is linked.

2. Behavior on ion-exchange resins. An unlinked mixture of RIg and PDM-PGA chromatographed on QAE or DEAE Sephadex with a gradient from 0.1 M Tris-HCL pH 6.5 to 1 M sodium chloride produces two elution peaks (a) excluded from the gel, the RIg peak (b) eluted at a peak of 0.43 sodium chloride, the PDM-PGA. In contrast, the PDM-PGA-RIg preparation shows a much diminished RIg peak and a shift of the second peak to 0.35 M.

3. Immunoelectrophoretic behavior. Electrophoresis of 2 1 of PDM-PGA-RIg on an agar-coated slide followed by diffusion with goat-anti-rabbit antiserum gives a precipitin line showing rabbit immunoglobulin present in material having marked anionic characteristics consistent with PDM-PGA. PDM-PGA itself gives no precipitin line.

4. Alkylating activity. By testing the material with nitrobenzyl pyridine in the manner described above, it is shown that the full alkylating activity of the drug-carrier is retained following linkage to globulin.

5. Analysis. The preparation thus contains the following amounts of drug, carrier and globulin:

| PDM | 3.1 mg/l | by U.V. spectroscopy |
|-----|----------|----------------------|
|     | 1.9 mg/ml | in terms of alkylating activity |
| PGA | 8 mg/ml | calculated from starting quantities |
| RIg | 10 mg/ml | |

The drug/carrier/globulin shows the following biological properties:

1. Antibody activity. Complement-dependent cytotoxicity is determined by the release of radioactive chromium from labelled mouse lymphoma cells. The titre of the PDM-PGA-RIg is 1 in 20 compared with 1 in 30 for unlinked RIg (both at 10 mg/ml starting concentration.

2. Cytostatic activity in vitro. The mouse lymphoma cells are maintained in tissue culture for two days in the presence of a range of concentrations of PDM-PGA-RIg. Cytostasis is determined by measuring inhibition of cellular tritiated thymidine incorporation during the last four hours of culture, in comparison with cells in the absence of drug complexes. The results of a typical experiment shown below give the percentage inhibition at four concentrations of the components.

| Concentrations | | % Inhibition with various preparations | | | |
|---|---|---|---|---|---|
| Drug (in terms of alkylating) activity µg/ml | Globulin µg/ml | RIg alone | PDM-PGA + normal rabbit Globulin | PDM-PGA + RIg | PDM-PGA-RIg complex |
| 120 | 624 | 56 | 58 | 76 | 83 |
| 60 | 312 | 28 | 25 | 58 | 67 |
| 30 | 156 | 14 | 18 | 38 | 54 |
| 15 | 78 | 8 | 9 | 28 | 43 |

For any given concentration, the PDM-PGA-RIg complex demonstrates greater cytostatic properties than the other materials.

3. Anti-tumor activity in vivo. Groups of five C57B1/6 strain mice are injected with $5 \times 10^4$ EL4 lymphoma cells intraperitoncally on day 0. At 24 hour intervals on days, 1,2,3 and 4; the mice are injected i.p with the drug-carrier-globulin complex and compared with mice similarly treated with various components of the complex. The survival times of the various groups are given below.

| Treatment | Dose per injection | | Median Survival time(MST) days | % increase in survival time compared with saline controls. | % mice surviving without evidence tumour at days 45 |
|---|---|---|---|---|---|
| | Drug (alkylating) activity µg | Globulin mg | | | |
| saline | — | — | 13 | — | 0 |
| RIg alone | — | 4 | 19 | 47% | 0 |
| PDM-PGA | 765 | — | 25 | 92% | 20 |
| PDM-PGA + RIg unlinked | 765 | 4 | 38 | 192% | 40 |
| PDM-PGA-RIg | 765 | 4 | >60 | >360% | 100 |

Thus doses of PDM-PGA and RIg when linked in the complex have greater antitumor activity than either component alone or the two components together but unlinked.

EXAMPLE 4

Goat anti-human melanoma Ig is prepared from a melanoma cell suspension containing $2.8 \times 10^7$ cells injected intraperitoneally into a young adult female goat. This injection is repeated four times at weekly intervals and then the animal is bled out one week after the final injection. Serum is separated from the blood and this is absorbed with 3g wet weight pooled human spleen cells/ml for 90 mins. at 4°. This absorption is repeated twice. The absorbed serum is then fractionated to yield Ig by a standard ammonium sulphate precipation method followed by dialysis.

P-[bis(2-chloroethyl)amino]phenylalanine-polyglutamic acid (m.w. 35,000) is prepared by methods described in Example 3 replacing p-[N,N-(bis-2-chloroethyl)]-phenylenediamine with p-[bis(2-chloroethyl)amino]phenylalanine and using equivalent quantities. To this polymer carrier cytotoxic drug is bound the above goat anti-human melanoma Ig.

Freeze dried p-[bis-(2-chloroethyl)amino]phenylalanine-polyglutamic acid (M.W. 35,000) is bound to the goat anti-human melanoma Ig by dissolving the polymer-carrier-cytotoxic drug complex in water to give a concentration of 120 mg/ml. 200 Mg of ethyl-3-(3-dimethylaminopropyl)carbodiimide is added to 10 ml of the polymer carrier-cytotoxic drug solution and when dissolved, the solution is diluted to 400 ml. with phosphate buffered saline, pH 72.

The dilute solution is added to 400 ml of a rapidly stirring solution of goat anti-melanoma Ig at 5 mg/ml containing 28.8 m 5M sodium acetate. The preparation is dialysed against sterile 0.9% NaCl for 19 hours with one change of saline after 16 hours. The volume after dialysis is 890 ml. The preparation is membrane-filter sterilized and analysed for drug and protein concentration:

Drug concentration by U.V. spectroscopy 697 μg/ml
Drug concentration (alkylating activity) 317 μg/ml
Protein concentration 2.25 mg/ml Substitution ratio (active drug molecules per Ig molecule) 70:1.

EXAMPLE 5

Using the procedure set out in Example 4 and using equivalent quantities, p-[N,N-bis(2-chloroethyl)]-phenylenediamine, 2-amino-N-[p-bis(2-chloroethyl)amino]-phenyl-3-hydroxypropionamide, and 2 -amino-N-[p-bis(2-chloroethyl)amino]phenyl-3-hydroxy-2-hydroxymethylpropionamide provides goat-anti-human melanoma Ig labeled with the respective cytotoxic agent. For instance, using p-[N,N-bis(2-chloroethyl)amino]phenyl-3-hydroxypropionamide and polyglutamic acid molecular weight 35,000 provides a cytotoxic agent having 20 molecules of cytotoxic drug/Ig.

EXAMPLE 6

40 Mg of polylysine M.W. 16,000 dissolved in 4 ml of 0.9% sodium chloride and 40 mg of methotrexate is dissolved in a similar amount of 0.9% sodium chloride by addition of 1N sodium hydroxide until a clear solution is obtained. The pH is adjusted to 7.0 and the methotrexate solution is added dropwise to the polylysine solution and then 40 mg of 1-ethyl-3(3-dimethylaminopropyl)carbodiimide is stirred in. The pH is lowered to 4 with hydrochloric acid and then returned to 7 with sodium hydroxide. The methotrexate-polylysine precipitates and 0.1 of citraconic anhydride is added and the pH maintained above 8 with sodium hydroxide. The methotrexate-polylysine precipitate gradually redissolves as citraconylation proceeds. The polymer carrier-cytotoxic drug complex is bound to Ig as described in Example 3.

EXAMPLE 7

Using equivalent quantities of polyethyleneimine (M.W. 20,000), 4-{p-[bis(2-chloroethyl)amino]phenyl}•butyric acid and 1-ethyl-3-(3-dimethylaminopropyl)carbodiimide as in Example 6, the cytotoxic drug is linked to the polymer carrier. Reaction with citraconic anhydride is not carried out with polyethyleneimine as it was with polylysine. To 40 mg of goat anti-human lymphoma Ig in 40 ml of buffer with the pH adjusted to 3 with hydrochloric acid is added dropwise 32 mg of the above polymer carrier-cytotoxic drug in 8 ml of buffer. The pH is maintaineed below 4. 20 Ml of 5% glutaraldehyde in saline is added and the pH is raised to 9.5 with 1N sodium hydroxide. The solution is held at that pH for 3-20 seconds and then returned to pH 3 by the addition of 1N hydrochloric acid. The process of addition and pH adjustment is repeated three times. The pH is then adjusted to 6 and the preparation dialysed against saline.

EXAMPLE 8

10 Mg. of polyethyleneimine (M.W. 20,000) is dissolved in 0.25 ml of water and the pH is adjusted to 7 with hydrochloric acid and 20 mg of cytosine arabinoside monophosphate is added and the pH is readjusted to 8, and then 20 mg of 1-ethyl-3-(3-dimethylaminopropyl)carbodiimide is added and the volume brought to 1 ml. This solution is allowed to stand for 16 hours at 20° C and protected from light. The preparation is dialysed against saline buffered to pH 7.3 with tris-acetate buffer (0.02M). This polymer carrier having cytotoxic drug bound to it may in turn be bound to Ig mentioned in Example 1 by the carbodiimide method or the glutaraldehyde method.

EXAMPLE 9

Cytosine arabinoside is linked through the amino group to polymer carriers such as polyglutamic acid and dextran activated with cyanogen bromide by methods set out in the earlier examples.

EXAMPLE 10

2.39 Parts of N-carbobenzyloxy-L-serine and 2.69 parts of p-[N,N-bis(2-chloroethyl)]phenylenediamine hydrochloride were stirred together at room temperature and in the dark as a suspension in 50 parts by volume of dry methylene chloride. Then distilled 1.01 parts of distilled triethylamine was added and stirring was continued for 30 minutes. A solution of 2.16 parts of N,N-dicycohexylcarbodiimide in 50 parts by volume of dry methylene was added over 10 minutes. Stirring was continued for 24 hours to provide a dark solution and a white precipitate. The reaction mixture was filtered and the filtrate was successively washed with aqueous sodium bicarbonate, 2 molar hydrochloric acid, and water. The organic layer was then dried over sodium sulfate and filtered and removal of solvent in vacuo provided a crude solid which after recrystallization from acetone/hexane or toluene provided 2 -carbobenzyloxyamino-N-[p-bis(2-chloroethyl)amino]phenyl-3-hydroxypropionamide, melting at 145°-146° and having the following structural formula

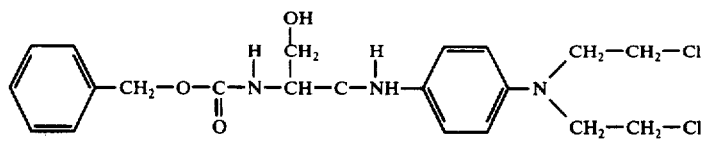

0.85 Parts of this material was dissolved in 85 parts by volume of distilled methanol containing 0.2 parts by volume of concentrated hydrochloric acid and the solution hydrogenated at room temperature and atmospheric pressure over 0.17 parts of a 5% palladium-oncharcoal calalyst. The catalyst was removed by filtration, the solvent removed in vacuo, and the product was precipitated upon addition of dry ether. 2-Amino-N-[p-bis(2-chloroethyl)amino]phenyl-3-hydroxypropionamide hydrochloride is isolated as a hydroscopic solid having the formula

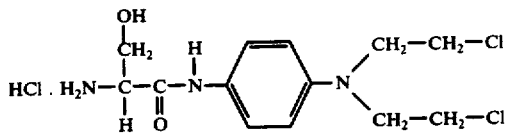

Replacement hydrochloric acid with an equivalent amount of sulfuric, phosphoric, hydrobromic, hydriodic, sulfamic, citric, lactic, maleic, malic, russinic, tartaric, cinnamic, acetic, benzoic, gluconic, ascorbic acid provide the corresponding acid addition salt. Neutralization of the acid salt with base and extraction with ether provides the free base, 2-amino-N-[p-bis(2-chloroethyl)amino]phenyl-3-hydroxypropionamide.

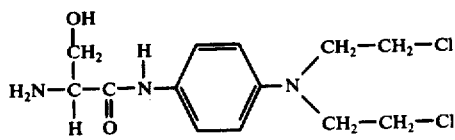

EXAMPLE 11

5.9 Parts of DL-serine was dissolved in 1100 parts by volume of 0.2 molar sodium carbonate. 5.6 parts by volume of a 1.0 molar cupric sulfate solution was then added, followed by 34 parts by volume of 40% aqueous formaldehyde solution. The solution was then heated at 95°-100° C for 20 minutes and a precipitate of copper resulted.

The reaction mixture was allowed to cool to room temperature and then filtered to remove the precipitated copper. After acidification with glacial acetic acid, the solution was concentrated under reduced pressure to around 100 parts by volume and then poured onto a Zeolite 225 ion exchange column, H form. This was washed with water until the acid band disappeared, when the column was eluted with 2M ammonium hydroxide, collecting and combining those fractions which gave a position ninhydrin reaction. These fractions were then concentrated in vacuo, when IMS (95% ethanol) was added to precipitate the required product. After standing at 0° C for 3 days the crude product was filtered off, washed with IMS, and then recrystalized from IMS/water to afford 2-amino-3-hydroxy-2-hydroxymethylpropionic acid, melting at 253°-254° C and having the following structural formula

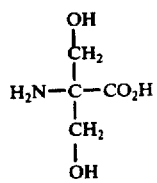

19.20 parts of this propionic acid is reacted with 21.56 parts by volume of N-benzylchloroformate in 236 parts by volume of N-benzylchloroformate in 236 parts by volume of sodium bicarbonate containing 29.8 parts of sodium carbonate. Following the procedure set out in Example 1, 2-carbobenzyloxyamino-3-hydroxy-2-hydroxymethylpropionic acid, melting at 109°-112° C (lit 112°-114°) is isolated. This compound has the following structural formula

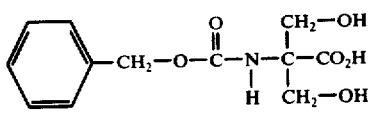

1.0 parts of this material were placed with 1.1 parts of p-[N,N-bis(2-chloroethyl)]phenylenediamine hydrochloride in 20 parts by volume of methylene chloride. 0.418 Parts of distilled triethylamine was added with continuing stirring and after stirring for 10 minutes 0.85 parts of N,N-dicyclohexylcarbodiimide in 20 parts by volume of dry methylene chloride was added over a 10 minute period. The reaction was worked up as in Example 1 to provide 2-carbobenzyloxyamino-N-[p-bis(2-chloroethyl)amino]phenyl-3-hydroxy-2-hydroxymethylpropionamide, melting at 138°-141° C, and having the following structural formula

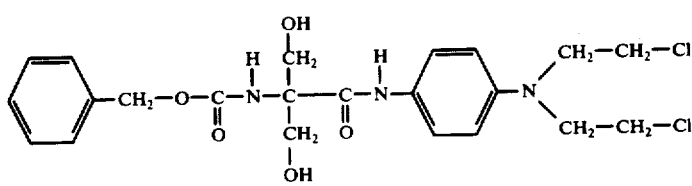

Using equivalent quantities and following the procedures in Example 1, 0.5 parts of this material is catalytically hydrogenated over 5% palladium-on-charcoal catalyst to provide 2-amino-N-[p-bis(2-chloroethyl)amino]phenyl-3-hydroxy-2-hydroxymethylpropionamide hydrochloride having the following structural formula

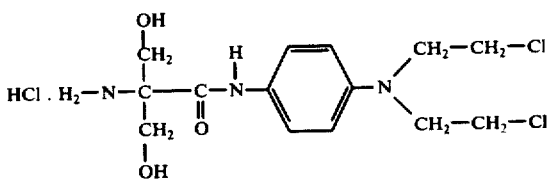

Other pharmaceutically acceptable acid addition salts and the free base 2-amino-N-[p-bis(2-chloroethyl)amino]phenyl-3-hydroxy-2-hydroxymethylpropionamide are prepared as described in Example 1.

Alternatively, 5.20 parts of 2-carbobenzyloxyamino-3-hydroxy-2-hydroxymethylpropionic acid and 5.95 parts of 1-hydroxy benzotriazole in 130 parts by volume of dry methylene chloride are reacted. To this reaction mixture was added 4.03 parts of N,N-dicyclohexylcarbodiimide and stirring continued for 16 hours. Then 5.7 parts of p-[N,N-bis(2-chloroethyl)]phenylenediamine hydrochloride and 2.99 parts by volume of triethylamine are added and stirred for 65 hours and worked up as earlier described to provide 2-carbobenzyloxyamino-N-[p-bis(2-chloroethyl)amino]-phenyl-3-hydroxymethylpropionamide.

What is claimed is:

1. A cytotoxic agent comprising an immunoglobulin specific for antigens on the surface of cells to be killed having 1-10 polymer carrier molecules convalently bound thereto, said polymer carrier having about 5-500 molecules of a cytotoxic drug covalently bound thereto and said polymer carrier having a molecular weight of 5000-500,000 and free carboxyl, amino or cycloimidocarbonate groups for covalently bonding, said cytotoxic drug also having amino or carboxyl groups available for covalent bonding.

2. A cyctotoxic agent according to claim 1 represented by the formula

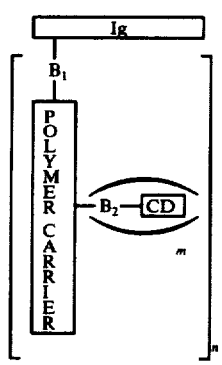

wherein Ig represents an immunoglobulin specific to antigens on the surface of cells to be killed; the polymer carrier has a molecular weight of 5000-500,000 and is selected from the group of polymers comprising:
a. dextran activated with cyanogen bromide to form cycloimidocarbonate and functionalized with —NH(CH$_2$)$_x$CO$_2$H, —NH—(CH$_2$)$_x$—NH$_2$, wherein $x$ is 3-8,
b. aminoethylated dextran,
c. polyglutamic acid,
d. polyaspartic acid,
e. polyarginine,
f. serum albumen,
g. fibrinogen,
h. γ-globulin,
h. polylysine (solubilized by reaction with citraconic anhydride),
j. copolymers of lysine-phenylalanine, lysinetryosine, and glutamic acid-tyrosine; CD represents a covalently bound cytotoxic drug selected from the group comprising:
p-[N,N-bis(2-chloroethyl)]phenylenediamine,
p-[bis(2-chloroethyl)amino]phenylalanine,
4-{p-[bis(2-chloroethyl)amino]phenyl}butyric acid,
2-amino-N-[p-bis(2-chloroethylamino]phenyl-3-hydroxypropionamide,
2-amino-N-[p-bis(2-chloroethyl)amine]phenyl-3-hydroxy-2-hydroxymethyl propionamide, N-{p{[(2,4-diamino-6-pteridinyl)methyl]methylamino}benzyl}-L-glutamic acid,
cytosine arabinoside, cytosine arabinoside monophosphate,
O-[N,N-bis(2-chloropropyl)]carbamoylglycollic acid,
daunomycin, doxorubicin, and diphtheria toxin;
B$_1$ represents a covalent bond between Ig and polymer carrier of the formula

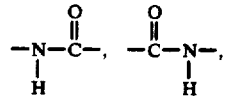

B$_2$ represents a covalent bond between the polymer carrier and CD of the formula

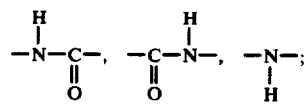

$m = 5-500$;
$n = 1-10$.

3. A cytotoxic agent according to claim 2 wherein the polymer carrier is dextran, molecular weight 5000-500,000, activated with cyanogen bromide to form cycloimidocarbonate and functionalized with 1,6-diaminohexane; CD represents covalently bound p-[N,N-bis(2-chloroethyl)]phenylenediamine, p-[bis(2-chloroethyl)amino]phenyl-3-hydroxypropionamide, or 2-amino-N-[p-bis(2-chloroethyl)amino]phenyl-3-hydroxy-2-hydroxymethyl propianamide;
B$_1$ represents —N=CH—(CH$_2$)$_3$—CH=N—;
B$_2$ represents

$m = 5-500$;
$n = 1-10$.

4. A cytotoxic agent according to claim 3 wherein the dextran has a molecular weight 5,000-50,000.

5. A cytotoxic agent according to claim 13 wherein the dextran has a molecular weight of about 17,000.

6. A cytotoxic agent according to claim 2 wherein the polymer carrier is polyglutamic acid, molecular weight 5000-500,000; CD represents covalently bound p-[N,N-bis(2-chloroethyl)]phenylenediamine, p-[bis(2-chloroethyl)amino]phenylalanine, 2-amino-N-[p-bis(2-chloroethyl)amino]phenyl-3-hydroxypropionamide, or 2-amino-N-[p-bis(2-chloroethyl)amino]phenyl-3-hydroxy-2-hydroxymethyl propionamide;
B$_1$ represents

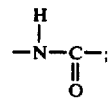

B$_2$ represents

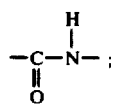

$m = 5-500$; and $n = 1-10$.

7. A cytotoxic agent according to claim 6 wherein the polyglutamic acid has a molecular weight of 5,000–100,000.

8. A cytotoxic agent according to claim 6 wherein the polyglutamic acid has a molecular weight of about 35,000.

9. A cytotoxic agent according to claim 2 wherein the polymer carrier is polylysine solubilized by reaction with citraconic anhydride and having a molecular weight of 5,000–100,000;

CD represents p-[bis(2-chloroethyl)amino[phenylalanine, 4-{p-[bis(2-chloroethyl)amino]phenyl}butyric acid, or N-{p{[2,4-diamino-6-pteridinyl)methyl]methylamino}benzyl}-L-glutamic acid;

$B_1$ is

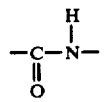

or $-N=CH-(CH_2)_3-CH=N-$;

$B_2$ is

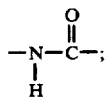

$m = 5-500$ and
$n = 1-10$.

10. A cytotoxic agent according to claim 2 wherein the polymer carrier is polyethyleneimine having a molecular weight of 5,000–500,000;

CD represents p-[bis(2-chloroethyl)amino]phenylalanine, 4-{p-[bis(2-chloroethyl)amino]phenyl}butyric acid or N-{p{[2,4-diamino-6-pteridinyl)methyl]methylamino}benzyl}-L-glutamic acid;

$B_1$ is

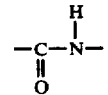

or $-N=CH-(CH_2)_3-CH=N-$;

$B_2$ is

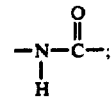

$m = 5-500$ and
$n = 1-10$.

11. A cytotoxic agent according to claim 10 wherein the polymer carrier is polyethyleneimine having a molecular weight of 5,000–100,000.

12. A cytotoxic agent according to claim 10 wherein the polymer carrier has a molecular weight of about 20,000.

13. A cytotoxic agent according to claim 1 represented by the formula

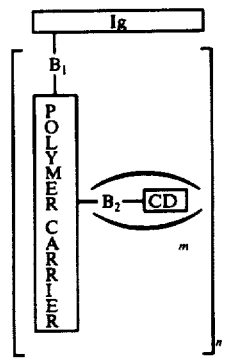

wherein the polymer carrier is polyglutamic acid of molecular weight 5000–500,000;

CD represents covalently bound p-[N,N-bis(2-chloroethyl)]phenylenediamine, p-[bis(2-chloroethyl)amino]phenylalanine, 2-amino-N-[p-bis(2-chloroethyl)amino]phenyl-3-hydroxypropionamide, or 2-amino-N-[p-bis(2-chloroethyl)amino]phenyl-3-hydroxy-2-hydroxymethyl propionamide;

$B_1$ represents

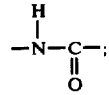

$B_2$ represents

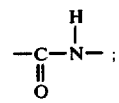

$m = 5-500$; and
$n = 1-10$.

* * * * *